(12) United States Patent
Masel et al.

(10) Patent No.: US 9,181,625 B2
(45) Date of Patent: Nov. 10, 2015

(54) DEVICES AND PROCESSES FOR CARBON DIOXIDE CONVERSION INTO USEFUL FUELS AND CHEMICALS

(71) Applicant: Dioxide Materials, Inc., Champaign, IL (US)

(72) Inventors: Richard I. Masel, Champaign, IL (US); Brian A. Rosen, Wilmington, DE (US); Wei Zhu, Champaign, IL (US)

(73) Assignee: Dioxide Materials, Inc., Boca Raton, FL (US)

(*) Notice: Subject to any disclaimer, the term of this patent is extended or adjusted under 35 U.S.C. 154(b) by 21 days.

(21) Appl. No.: 14/035,935

(22) Filed: Sep. 24, 2013

(65) Prior Publication Data

US 2014/0093799 A1 Apr. 3, 2014

Related U.S. Application Data

(60) Provisional application No. 61/705,042, filed on Sep. 24, 2012.

(51) Int. Cl.
*C25B 11/06* (2006.01)
*C25B 11/04* (2006.01)
(Continued)

(52) U.S. Cl.
CPC . *C25B 11/04* (2013.01); *C25B 1/00* (2013.01); *C25B 3/00* (2013.01); *C25B 3/04* (2013.01); *C25B 9/08* (2013.01); *C25B 11/0473* (2013.01); *G01N 27/30* (2013.01); *G01N 27/302* (2013.01); *G01N 33/004* (2013.01)

(58) Field of Classification Search
None
See application file for complete search history.

(56) References Cited

U.S. PATENT DOCUMENTS 1,919,850 A 7/1933 Luscher
2,511,198 A 6/1950 Engel
(Continued)

FOREIGN PATENT DOCUMENTS

CA 1272180 A 7/1990
CA 2821642 A1 6/2012
(Continued)

OTHER PUBLICATIONS

Arenz, M. et al., "The effect of the particle size on the kinetics of CO electrooxidation on high surface area Pt catalysts", Journal of the American Chemical Society 127 (2005), pp. 6819-6829.
(Continued)

*Primary Examiner* — Patrick Ryan
*Assistant Examiner* — Wyatt McConnell
(74) *Attorney, Agent, or Firm* — Corridor Law Group, P.C.

(57) ABSTRACT

Electrochemical devices for converting carbon dioxide to useful reaction products include a solid or a liquid with a specific pH and/or water content. Chemical processes using the devices are also disclosed, including processes to produce CO, HCO$^-$, H$_2$CO, (HCO$_2$)$^-$, H$_2$CO$_2$, CH$_3$OH, CH$_4$, C$_2$H$_4$, CH$_3$CH$_2$OH, CH$_3$COO$^-$, CH$_3$COOH, C$_2$H$_6$, (COOH)$_2$, (COO$^-$)$_2$, acrylic acid, diphenyl carbonate, other carbonates, other organic acids and synthetic fuels. The electrochemical device can be a CO$_2$ sensor.

25 Claims, 5 Drawing Sheets

(51) Int. Cl.
| | | |
|---|---|---|
| G01N 27/30 | (2006.01) | |
| C25B 1/00 | (2006.01) | |
| C25B 3/00 | (2006.01) | |
| C25B 3/04 | (2006.01) | |
| C25B 9/08 | (2006.01) | |
| G01N 33/00 | (2006.01) | |

(56) References Cited

U.S. PATENT DOCUMENTS

| | | |
|---|---|---|
| 2,996,359 A | 8/1961 | Mossman et al. |
| 3,959,094 A | 5/1976 | Steinberg |
| 4,207,151 A | 6/1980 | Franke et al. |
| 4,240,882 A | 12/1980 | Ang et al. |
| 4,315,753 A | 2/1982 | Bruckenstein et al. |
| 4,474,652 A | 10/1984 | Brown et al. |
| 4,523,981 A | 6/1985 | Ang et al. |
| 4,545,872 A | 10/1985 | Sammells et al. |
| 4,595,465 A | 6/1986 | Ang et al. |
| 4,608,132 A | 8/1986 | Sammells |
| 4,608,133 A | 8/1986 | Morduchowitz et al. |
| 4,609,440 A | 9/1986 | Frese, Jr. et al. |
| 4,609,441 A | 9/1986 | Frese, Jr. et al. |
| 4,620,906 A | 11/1986 | Ang |
| 4,668,349 A | 5/1987 | Cuellar et al. |
| 4,673,473 A | 6/1987 | Ang et al. |
| 4,756,807 A | 7/1988 | Meyer et al. |
| 4,771,708 A | 9/1988 | Douglass, Jr. |
| 4,789,442 A | 12/1988 | Nakagawa et al. |
| 4,818,353 A | 4/1989 | Langer et al. |
| 4,879,070 A | 11/1989 | Kent |
| 4,968,393 A | 11/1990 | Mazur et al. |
| 5,064,733 A | 11/1991 | Krist et al. |
| 5,071,526 A | 12/1991 | Pletcher et al. |
| 5,089,661 A | 2/1992 | Maspero et al. |
| 5,206,433 A | 4/1993 | Hohenschutz et al. |
| 5,284,563 A | 2/1994 | Fujihira et al. |
| 5,294,740 A | 3/1994 | Kiefer et al. |
| 5,334,759 A | 8/1994 | Lippert et al. |
| 5,382,332 A | 1/1995 | Fujihira et al. |
| 5,639,910 A | 6/1997 | Ikariya et al. |
| 5,709,789 A | 1/1998 | Shay et al. |
| 5,763,622 A | 6/1998 | Podszun et al. |
| 5,804,045 A | 9/1998 | Orillon et al. |
| 5,879,915 A | 3/1999 | Loubiere et al. |
| 5,928,806 A | 7/1999 | Olah et al. |
| 5,952,540 A | 9/1999 | Lee et al. |
| 6,024,855 A | 2/2000 | Sharifian et al. |
| 6,429,333 B1 | 8/2002 | Saari et al. |
| 6,660,680 B1 | 12/2003 | Hampden-Smith et al. |
| 6,706,657 B2 | 3/2004 | Commereuc et al. |
| 6,713,649 B1 | 3/2004 | Hladiy et al. |
| 6,841,700 B2 | 1/2005 | Auer et al. |
| 6,849,764 B2 | 2/2005 | Gurkaynak et al. |
| 6,867,329 B2 | 3/2005 | Auer et al. |
| 6,906,222 B2 | 6/2005 | Slany et al. |
| 6,955,743 B2 | 10/2005 | Rousu et al. |
| 6,987,134 B1 | 1/2006 | Gagnon |
| 6,992,212 B2 | 1/2006 | Zehner et al. |
| 7,081,547 B2 | 7/2006 | Fujimoto et al. |
| 7,157,404 B1 | 1/2007 | Jun et al. |
| 7,241,365 B2 | 7/2007 | Auer et al. |
| 7,253,316 B2 | 8/2007 | Pastre et al. |
| 7,323,593 B2 | 1/2008 | Adami et al. |
| 7,351,860 B2 | 4/2008 | Adami et al. |
| 7,420,088 B2 | 9/2008 | Karl et al. |
| 7,459,590 B2 | 12/2008 | Olah et al. |
| 7,479,570 B2 | 1/2009 | Ogo et al. |
| 7,605,293 B2 | 10/2009 | Olah et al. |
| 7,608,743 B2 | 10/2009 | Olah et al. |
| 7,612,233 B2 | 11/2009 | Hauk et al. |
| 7,618,725 B2 | 11/2009 | Masel et al. |
| 7,704,369 B2 | 4/2010 | Olah et al. |
| 8,313,634 B2 | 11/2012 | Bocarsly et al. |
| 8,592,633 B2 | 11/2013 | Cole et al. |
| 2004/0031685 A1 | 2/2004 | Anderson et al. |
| 2006/0096871 A1 | 5/2006 | Manoukian et al. |
| 2006/0234174 A1 | 10/2006 | Burrahm et al. |
| 2006/0235091 A1 | 10/2006 | Olah et al. |
| 2007/0036706 A1 | 2/2007 | Ogo et al. |
| 2007/0045125 A1 | 3/2007 | Hartvigsen et al. |
| 2007/0187247 A1 | 8/2007 | Lackner et al. |
| 2008/0039538 A1 | 2/2008 | Olah et al. |
| 2008/0103040 A1 | 5/2008 | Rodriguez et al. |
| 2008/0223727 A1 | 9/2008 | Oloman et al. |
| 2009/0014336 A1 | 1/2009 | Olah et al. |
| 2009/0016948 A1 | 1/2009 | Young |
| 2009/0169452 A1 | 7/2009 | Constantz et al. |
| 2009/0289211 A1 | 11/2009 | Fujioka et al. |
| 2010/0132556 A1 | 6/2010 | Constantz et al. |
| 2010/0133120 A1 | 6/2010 | Varney et al. |
| 2010/0135865 A1 | 6/2010 | Constantz et al. |
| 2010/0137457 A1 | 6/2010 | Kaplan |
| 2010/0187123 A1 | 7/2010 | Bocarsly et al. |
| 2010/0193370 A1 | 8/2010 | Olah et al. |
| 2010/0276287 A1 | 11/2010 | Manoukian et al. |
| 2011/0114501 A1 | 5/2011 | Teamey et al. |
| 2011/0114502 A1 | 5/2011 | Cole et al. |
| 2011/0114503 A1 | 5/2011 | Sivasankar et al. |
| 2011/0114504 A1 | 5/2011 | Sivasankar et al. |
| 2011/0226632 A1 | 9/2011 | Cole et al. |
| 2011/0237830 A1 | 9/2011 | Masel |

FOREIGN PATENT DOCUMENTS

| | | |
|---|---|---|
| DE | 183856 C | 1/1906 |
| EP | 0012215 | 6/1980 |
| EP | 0293230 A | 11/1988 |
| EP | 0323300 A | 7/1989 |
| GB | 2230782 A | 10/1990 |
| JP | 201217300 | 1/2012 |
| WO | 2008110830 A | 9/2008 |
| WO | 2010007602 A | 1/2010 |
| WO | 2010063626 A | 6/2010 |
| WO | 2011120021 A | 9/2011 |
| WO | 2012006240 A | 1/2012 |
| WO | 2013006711 | 10/2013 |

OTHER PUBLICATIONS

Azuma, M. et al., "Electrochemical reduction of carbon dioxide on various metal, electrodes in low-temperature aqueous KHCO3 media", J. Electrochem. Soc. 137 (1990), pp. 1772-1778.

Barrosse-Antle, L. et al., "Reduction of carbon dioxide in 1-butyl-3-methylimidazolium acetate", Chem. Commun. (2009), pp. 3744-3746.

Begum, A. et al., "Electrocatalysis of CO2 reduction by ruthenium benzothiazole and bithiazole complexes", Electrochemistry Communications 9 (2007), pp. 2525-2528.

Bell, A.T., "Basic Research Needs: Catalysis for Energy", U.S. Department of Energy Report PNNL-17214 (2008), p. 69.

Blizanac, B. et al., "Oxygen Reduction on Silver Low-Index Single-Crystal in Alkaline Solution: Rotating Ring DiskAg (hkl)", J. Phys. Chem. 110 (2006), pp. 4735-4741.

Bregoli, L., "The influence of platinum crystallite size on the electrochemical reduction of oxygen in phosphoric acid", Electrochimica Acta 23 (1978), pp. 489-492.

Cahill, L. et al., "Investigation of proton dynamics and the proton transport pathway in choline dihydrogen phosphate using solid-state NMR", Physical Chemistry Chemical Physics 12 (2010), pp. 5431-5438.

Chandrasekaran, K. et al., "In-situ spectroscopic investigation of adsorbed intermediate radicals in electrochemical reactions: carbon dioxide CO2- on platinum", Surface Science 185 (1987), pp. 495-514.

Chaplin, R. et al., "Effects of process conditions and electrode material on reaction pathways for carbon dioxide electroreduction with particular reference to formate formation", Journal of Applied Electrochemistry 33 (2003), pp. 1107-1123.

Chen, Q. et al., "Role of surface defect sites: From Pt model surfaces to shape-controlled nanoparticles", Chemical Science 3 (2012), pp. 136-147.

(56) References Cited

OTHER PUBLICATIONS

Cherstiouk, O. et al., "Model approach to evaluate particle size effects in electrocatalysis: Preparation and properties of Pt nanoparticles supported on GC and HOPG", Electrochimica Acta 48 (2003), pp. 3851-3860.
Cheung, K.C. et al., "Electrocatalytic reduction of carbon dioxide by a polymeric film of rhenium tricarbonyl dipyridylamine", Journal of Organometallic Chemistry 694 (2009), pp. 2842-2845.
Chu, D. et al., "Fixation of CO2 by electrocatalytic reduction and electropolymerization in ionic liquid-H2O solution", Chem. Sus. Chem. 1 (2008), pp. 205-209.
Cole, E. et al., "Using a one-electron shuttle for the multielectron reduction of CO2 to methanol: kinetic, mechanism, and structural insights", J. Am. Chem. Soc. 132 (2010), pp. 11539-11551.
Danly, D., "Development and commercialization of the Monsanto electrochemical adiponitrile process", J. Electrochemical Soc. 131 (1984), pp. 435C-442C.
Davis, Jr., J.H. et al., "Commercially available salts as building blocks for new ionic liquids", ACS Symp. Ser. 856 (2003), pp. 100-107.
Delacourt, C. et al., "Design of an electrochemical cell making syngas (CO+H2-) from CO2 and H2O reduction at room temperature", Journal of the Electrochemical Society 155 (2008), pp. B42-B49.
Delacourt, C. et al., "Mathematical modeling of a cation-exchange membrane containing two cations", Journal of the Electrochemical Society 155 (2008), pp. B1210-B1217.
Derien, S. et al., "Activation of carbon dioxide: nickel-catalyzed electrochemical carboxylation of diynes", J. Organic Chem. vol. 58. No. 9 (1993), pp. 2578-2588.
DeWulf, D.W. et al., "Electrochemical and surface studies of carbon dioxide reduction to methane and ethylene at copper electrodes in aqueous solutions", Journal of the Electrochemical Society 136 (1989), pp. 1686-1691.
DeWulf, D.W. et al., "The electrochemical reduction of CO2 to CH4 and C2H4 at Cu/Nafion electrodes (solid polymer electrolyte structures)", Catalysis Letters 1 (1988), pp. 73-80.
Dietz, H. et al., "Influence of substituted benzaldehydes and their derivatives as inhibitors for hydrogen evolution in lead/acid batteries", Journal of Power Sources 53 (1995), pp. 359-365.
Dube, P. et al., "Influence of adsorption processes on the CO2 electroreduction: An electrochemical mass spectrometry study", Journal of Electroanalytical Chemistry 582 (2005), pp. 230-240.
DuBois, D. in A. Bard, ed., "Encyclopedia of Electrochemistry", 7a, Springer (2006), pp. 202-225.
DuBois, D. et al., "Electrochemical reduction of carbon dioxide catalyzed by [Pd(triphosphine)(solvent)](BF4)2 complexes: synthetic and mechanistic studies", J. Am. Chem. Soc., vol. 113. No. 23 (1991), pp. 8753-8764.
Eggins, B.R. et al., "Improved yields of oxalate, glyoxylate and glycolate from the electrochemical reduction of carbon dioxide in methanol", Journal of Applied Electrochemistry 27 (1997), pp. 706-712.
Eggins, B.R. et al., "Voltammetry of carbon dioxide. Part 1. A general survey of voltammetry at different electrode materials in different solvents", J. Electroanalytical Chem. 148 (1983), pp. 17-24.
Fisher, B. et al., "Electrocatalytic reduction of carbon dioxide by using macrocycles of nickel and cobalt", J. Am. Chem. Soc., vol. 102, No. 24 (1980), pp. 7361-7363.
Franklin, T.C. et al., "The effect of quaternary ammonium salts on the anodic oxidation of ethanol", Surface Technology 24 (1985), pp. 143-155.
Fukuzumi, S.,"Bioinspired Energy Conversion Systems for Hydrogen Production and Storage", Eur. J. Inorg. Chem., vol. 2008. No. 9. (2008), pp. 1351-1362.
Furuya, N. et al., "High performance Ru-Pd catalysts for CO2 reduction at gas-diffusion electrodes", Journal of Electroanalytical Chemistry 431 (1997), pp. 39-41.

Gattrell, M. et al. "A review of the aqueous electrochemical reduction of CO2 to hydrocarbons at copper", Journal of Electroanalytical Chemistry 594 (2006), pp. 1-19.
Gattrell, M. et al., "Electrochemical reduction of CO2 to hydrocarbons to store renewable electrical energy and upgrade biogas", Energy Conversion Management 48 (2007), pp. 1255-1265.
Haerens, K. et al., "Electrochemical decomposition of choline chloride based ionic liquid analogues", Green Chemistry 11 (2009), pp. 1357-1365.
Himeda, Y., "Conversion of CO2 into formate by homogeneously catalyzed hydrogenation in water: tuning catalytic activity and water solubility through the acid-base equilibrium of the ligand", European Journal of Inorganic Chemistry (2007), pp. 3927-3941.
Hori, Y. et al., "Electrochemical evidence of intermediate formation of adsorbed carbon monoxide in cathodic reduction of carbon dioxide at a nickel electrode", Electrochimica Acta 35 (1990), pp. 1777-1780.
Hori, Y. et al., "Electrochemical reduction of carbon dioxide at various series of copper single crystal electrodes", Journal of Molecular Catalysis A: Chemical 199 (2003), pp. 39-47.
Hori, Y., "Electrochemical CO2 reduction on metal electrodes", Modern Aspects of Electrochemistry 42 (2008), pp. 89-189.
Hoshi, N. et al., "Electrochemical reduction of carbon dioxide at a series of platinum single crystal electrodes", Electrochimica Acta 45 (2000), pp. 4263-4270.
Hoshi, N. et al., "Electrochemical reduction of carbon dioxide on kinked stepped surfaces of platinum inside the stereographic triangle", Journal of Electroanalytical Chemistry 540 (2003), pp. 105-110.
Hoshi, N. et al., "Electrochemical reduction of CO2 on single crystal electrodes of Ag(111), Ag(100), and Ag(110)", Journal of Electroanalytical Chemistry 440 (1997), pp. 283-286.
Ikeda, S. et al., "Electrochemical reduction of carbon dioxide using gas diffusion electrodes loaded with fine catalysts", Nanoscience and Nanotechnology (2008), pp. 108-113.
Ikeda, S. et al., "Zinc ion effect on electrochemical reduction of carbon dioxide at zinc electrode in aqueous solutions", Electrochemistry (Tokyo) 67 (1999), pp. 27-33.
Innocent, B. et al., "Electro-reduction of carbon dioxide to formate on lead electrode in aqueous medium", Journal of Applied Electrochemistry 39 (2009), pp. 227-232.
International Search Report and Written Opinion of the International Searching Authority issued on Oct. 31, 2011, in connection with PCT/US2011/042809.
International Search Report issued on Jul. 6, 2011, in connection with PCT/2011/030098.
Jiang, T. et al., "Solvent-free synthesis of substituted ureas from CO2 and amines with a functional ionic liquid as the catalyst", Green Chem. 10 (2008), pp. 465-469.
Jitaru, M., "Electrochemical carbon dioxide reduction—Fundamental applied topics (Review)", Journal of the University of Chemical Technology and Metallurgy 42 (2007), pp. 333-344.
Kabbabi, A. et al., "Particle size effect for oxygen reduction and methanol oxidation on Pt/C inside a proton exchange membrane", Journal of Electroanalytical Chemistry 373 (1994), pp. 251-254.
Saeki, T. et al., "Electrochemical reduction of CO2 with high current density in a CO2+methanol medium at various metal electrodes", Journal of Electroanalytical Chemistry 404 (1996), pp. 299-302.
Saeki, T. et al., "Electrochemical reduction of liquid CO2. Drastic enhancement of current density", Journal of the Electrochemical Society 141 (1994), pp. L130-L132.
Scheijen, F. et al., "The electrooxidation of small organic molecules on platinum nanoparticles supported on gold: Influence of platinum deposition procedure", Journal of Solid State Electrochemistry 12 (2008), pp. 483-495.
Seshadri, G. et al., "A new homogeneous electrocatalyst for the reduction of carbon dioxide to methanol at low overpotential", J. Electroanalytical Chemistry 372 (1994), pp. 145-150.
Silvester, D.S. et al., "Electrochemical reduction of benzoic acid and substituted benzoic acids in some room temperature ionic liquids", The Journal of Physical Chemistry C 112 (2008), pp. 12966-12973.

(56) References Cited

OTHER PUBLICATIONS

Silvester, D.S. et al., "Electrochemistry in room temperature ionic liquids: A review and some possible applications", Z. Phys. Chem. 220 (2006), pp. 1247-1274.

Singh, P. et al., "Comparison of Oxygen Reduction Reaction at Silver Nanoparticles and Polycrystalline Silver Electrodes in Alkaline Solution", J. Phys. Chem. 116 (2012), pp. 10656-10663.

Smolinka, T. et al., "$CO_2$ reduction on Pt electrocatalysts and its impact on $H_2$ oxidation in $CO_2$ containing fuel cell feed gas—A combined in situ infrared spectroscopy, mass spectrometry and fuel cell performance study", Electrochimica Acta 50 (2005), pp. 5189-5199.

Smolinski, S. et al., "Effect of surface order on adsorption of sulfate ions on silver electrodes", Journal of Electroanalytical Chemistry 442 (1998), pp. 41-47.

Sobkowski, J. et al., "Interaction of sulfate ions with monocrystalline silver electrodes", Colloids Surfaces A: Physicochem. Eng. Aspects 134 (1998), pp. 39-45.

Solla-Gullon, J. et al., "Co monolayer oxidation on semi-spherical and preferentially oriented (1 0 0) and (1 1 1) platinum nanoparticles", Electrochemistry Communications 8 (2006), pp. 189-194.

Solla-Gullon, J. et al., "Shape dependent electrocatalysis", Annual Reports on the Progress of Chemistry—Section C 107 (2011), pp. 263-297.

Solla-Gullon, J. et al., "Shape-dependent electrocatalysis: Methanol and formic acid electrooxidation on preferentially oriented Pt nanoparticles", Physical Chemistry Chemical Physics 10 (2008), pp. 3689-3698.

Star, A. et al., "Nanoelectric carbon dioxide sensors", Advanced Materials 16 (2004), pp. 2049-2051.

Subramanian, K. et al., "Electrochemical membrane reactor for the reduction of carbon dioxide to formate", Journal of Applied Electrochemistry 37 (2007), pp. 255-260.

Sun, J. et al., "Hydroxyl-functionalized ionic liquid: a novel efficient catalyst for chemical fixation of $CO_2$ to cyclic carbonate", Tetrahedron Letters 49 (2008), pp. 3588-3591.

Sung, Y.-E. et al., "Structure of chemisorbed sulfur on a Pt(III) electrode", Journal of the American Chemical Society 119 (1997), pp. 194-200.

Takahashi, I. et al., "Electrochemical reduction of $CO_2$ at copper single crystal Cu(S)-[n(111) Ã—(111)] and Cu(S)-[n(110) Ã—(100)] electrodes", Journal of Electroanalytical Chemistry 533 (2002), pp. 135-143.

Tian, N. et al., "Direct electrodeposition of tetrahexahedral Pd nanocrystals with high-index facets and high catalytic activity for ethanol electrooxidation", Journal of the American Chemical Society 132 (2010), pp. 7580-7581.

Tian, N. et al., "Platinum metal catalysts of high-index surfaces: from single-crystal planes to electrochemically shape-controlled nanoparticles", Journal of Physical Chemistry C112 (2008), pp. 19801-19817.

Tian, N. et al., "Synthesis of tetrahexahedral platinum nanocrystals with high-index facets and high electro-oxidation activity", Science 316 (2007), pp. 732-735.

Udupa, K.S. et al., "Electrolytic reduction of carbon dioxide to formic acid", Electrochimica Acta 16 (1971), pp. 1593-1598.

Welton, T., "Room-Temperature Ionic Liquids. Solvents for Synthesis and Catalysis". Chem. Revs., vol. 99, No. 8 (1999), pp. 2071-2083.

Wong, W.L. et al., "A robust ionic liquid as reaction medium and efficient organocatalyst for carbon dioxide fixation", Chem. Sus. Chem. 1 (2008), pp. 67-70.

Written Opinion of the International Searching Authority issued on Sep. 26, 2012, in connection with PCT/US2011/030098.

Xu, X. et al., "Effects of imidazolium salts as cocatalysts on the copolymerization of $CO_2$ with epoxides catalyzed by (salen)CrIIICl complex", Polymer 48 (2007), pp. 3921-3924.

Yan, T. et al., "Adsorption of $CO_2$ on the rutile (110) surface in ionic liquid. A molecular dynamics simulation", J. Phys. Chem. C 113 (2009), pp. 19389-19392.

Yang, H. et al., "Electrochemical activation of carbon dioxide in ionic liquid: synthesis of cyclic carbonates at mild reaction conditions", Chem. Commun. (2002), pp. 274-275.

Yano, H. et al., "Particle-size effect of nanoscale platinum catalysts in oxygen reduction reaction: An electrochemical and 195Pt EC-NMR study", Physical Chemistry Chemical Physics 8, 4932-4939 (2006).

Yano, H. et al., "Selective electrochemical reduction of $CO_2$ to ethylene at a three-phase interface on copper(I) halide-confined Cu-mesh electrodes in acidic solutions of potassium halides", Journal of Electroanalytical Chemistry 565 (2004), pp. 287-293.

Yano, J. et al., "Selective ethylene formation by pulse-mode electrochemical reduction of carbon dioxide using copper and copper-oxide electrodes", Journal of Solid State Electrochemistry 11 (2006), pp. 554-557.

Yano, M. et al., "Effects of additives in zinc alloy powder on suppressing hydrogen evolution", Journal of Power Sources 74 (1998), pp. 129-134.

Yoshizawa-Fujita, M. et al., "A new class of proton-conducting ionic plastic crystals based on organic cations and dihydrogen phosphate", Electrochemistry Communications 9 (2007), pp. 1202-1205.

Yu, D. et al., "Carboxylation of Terminal Alkynes with Carbon Dioxide Catalyzed by Poly(N-Heterocyclic Carbene)-Supported Silver Nanoparticles", Adv. Synth. Catal. 354 (2012), pp. 969-974.

Yuan, D. et al., "Electrochemical activation of carbon dioxide for synthesis of dimethyl carbonate in an ionic liquid", Electrochimica Acta 54 (2009), pp. 2912-2915.

Zhang, L. et al., "Electrochemical activation of $CO_2$ in ionic liquid (BMIMBF4): synthesis of organic carbonates under mild conditions", Green Chemistry 10 (2008), pp. 202-206.

Zhang, S. et al., "Chiral ionic liquids improved the asymmetric cycloaddition of $CO_2$ to epoxides", Green Chem. 11 (2009), pp. 935-938.

Zhang, Z. et al., "Hydrogenation of carbon dioxide is promoted by a task-specific ionic liquid", Angew. Chem. Int. Ed. 47 (2008), pp. 1127-1129.

Zhang, Z. et al., "Hydrogenation of $CO_2$ to formic acid promoted by a diamine-functionalized ionic liquid", Chem. Sus. Chem. 2 (2009), pp. 234-238.

Zhao, G. et al., "Electrochemical reduction of supercritical carbon dioxide in ionic liquid 1-n-butyl-3-methylimidazolium hexafluorophosphate", Journal of Supercritical Fluids 32 (2004), pp. 287-291.

Zhou, W. et al., "Size effects in electronic and catalytic properties of unsupported palladium nanoparticles in electrooxidation of formic acid", Journal of Physical Chemistry B 110 (2006), pp. 13393-13398.

Zhu, A., "Supported cholinechloride/urea as a heterogeneous catalyst for chemical fixation of carbon dioxide to cyclic carbonates", Green Chemistry. vol. 9 (2007), pp. 169-172.

International Search Report and Written Opinion issued on Feb. 15, 2013 in connection with PCT/US2012/043651.

Ikeda, S. et al., "Selective Formation of Formic Acid, Oxalic Add, and Carbon Monoxide by Electrochemical Reduction of Carbon Dioxide", Bull. Chem. Soc. Japan, vol. 60, (1987), pp. 2517-2522.

International Preliminary Report on Patentability issued on Jan. 3, 2013 in connection with International Application No. PCT/US2011/030098521.

Kaneco, S. et al., "Electrochemical conversion of carbon dioxide to formic acid on Pb in KOH/methane electrolyte at ambient temperature and pressure", Energy, vol. 23, No. 12 (1998), pp. 1107-1112.

Ogura, K. et al., "Selective formation of ethylene from C02 by catalytic electrolysis at a three-phase interface", Catalysis Today 98 (2004), pp. 515-521.

Scibioh, M. et al., "Electrochemical Reduction of Carbon Dioxide: A Status Report", Indian Natn. Sci. Acad., vol. 70, A, No. 3, (2004), pp. 407-462.

Third-Party Submissions Under 37 CFR 1.290, submitted on Sep. 17 and 18, 2013, in connection with co-owned U.S. Appl. No. 12/830,338, and Concise Description of Relevance for each of the references cited in the Third Party Submissions.

(56) References Cited

OTHER PUBLICATIONS

International Preliminary Report on Patentability issued on Jan. 9, 2014 in connection with International Application PCT/US2012/043651.
Urey, H. et al., "Some reactions of atomic hydrogen", Journal of the American Chem. Society 51 (1929), pp. 3286-3290.
Weiss, A. et al., "Formose sugars from formaldehyde", Applied Catalysis 1 (1981), pp. 237-246.
Idriss, H. et al., "Two routes to formaldehyde from formic acid on TiO2, (001) surfaces", Surface Science 348 (1996), pp. 39-48.
Kiss, G. et al., "Palladium-catalyzed reppe carbonylation", Chem. Rev. 101 (2001), pp. 3435-3456.
Jessop, P. et al., "Recent advances in the homogeneous hydrogenation of carbon dioxide", Coordination Chem. Rev. 248 (2004), pp. 2425-2442.
Gazsi, A. et al., "Decomposition and reforming of formic acid on supported Au catalysts: Production of CO-free H2", Journal of Physical Chem. C 115 (2011), pp. 15459-15466.
Sabatier, P. et al., "Chimie Organique.—Sur la decomposition catalytique de l'acide formique", Comptes Rendus Hebdomadaires Des Seances De L'Academie Dessciences 152 (2011), pp. 1213-1215.
Deng, J. et al., "Linked strategy for the production of fuels via formose reaction", Scientific Reports 3 (2013), p. 1244.
International Search Report and Written Opinion issued on Jun. 17, 2014 in connection with PCT/US2014/018067.
Chinese Office Action issued on Aug. 5, 2014 in connection with Chinese Application No. 201180023851.2.
D. Dubois, "Electrochemical Reactions of Carbon Dioxide", Encyclopedia of Electrochemistry, pp. 212 (2007).
International Search Report and Written Opinion issued on May 16, 2014 in connection with PCT/US2013/061506.
Kaneco, S. et al. "Effect of sodium cation on the electrochemical reduction of CO2 at a copper electrode in methanol", Journal of Solid State Electrochemistry 11 (2007), pp. 490-495.
Kaneco, S. et al., "Carbon dioxide sequestration technology by electrochemical conversion at cadmium electrode in methanol under mild conditions", Photo/Electrochemistry & Photobiology in Environment, Energy and Fuel (2003), pp. 181-189.
Kaneco, S. et al., "Electrochemical reduction of carbon dioxide to ethylene at a copper electrode in methanol using potassium hydroxide and rubidium hydroxide supporting electrolytes", Electrochimica Acta 51 (2006), pp. 3316-3321.
Kaneco, S. et al., "Electrochemical reduction of carbon dioxide to ethylene with high Faradaic efficiency at a Cu electrode in CsOH/methanol", Electrochimica Acta 44 (1999), pp. 4701-4706.
Kaneco, S. et al., "Electrochemical reduction of CO2 in copper particle-suspended methanol", Chemical Engineering Journal 119 (2006), pp. 107-112.
Kaneco, S. et al., "Electrochemical reduction of CO2 to Methane at the Cu electrode in methanol with sodium supporting salts and its comparison with other alkaline salts", Energy & Fuels 20 (2006), pp. 409-414.
Kaneco, S. et al., "Photoelectrochemical reduction of CO2 at p-InP electrode in copper particle-suspended methanol", Chemical Engineering Journal 148 (2009), pp. 57-62.
Kinge, S. et al., "Dependence of CO oxidation on Pt nanoparticle shape: A shape-selective approach to the synthesis of PEMFC catalysts", Applied Organometallic Chemistry 22 (2008), pp. 49-54.
Kinoshita, K., "Particle size effects for oxygen reduction on highly dispersed platinum in acid electrolytes", Journal of the Electrochemical Society 137 (1990), pp. 845-848.
Koleli, F. et al., "Reduction of CO2 under high pressure and high temperature on Pb-granule electrodes in a fixed-bed reactor in aqueous medium", Applied Catalysis A—General 274 (2004), pp. 237-242.
Koper, M., "Structure sensitivity and nanoscale effects in electrocatalysis", Nanoscale 3 (2011), pp. 2054-2073.
Laitar, D.S. et al., "Efficient homogeneous catalysis in the reduction of CO2 to CO", Journal of the American Chemical Society 127 (2005), pp. 17196-17197.
Lee, C.W. et al., "Studies on suppression of hydrogen evolution reaction for zinc/air fuel cell", Material Science Forums 539-543 (2007), pp. 1427-1430.
Li, H. et al., "Development of a continuous reactor for the electroreduction of carbon dioxide to formate—Part 1: Process variables", Journal of Applied Electrochemistry 36 (2006), pp. 1105-1115.
Li, H. et al., "Development of a continuous reactor for the electroreduction of carbon dioxide to formate—Part 2: Scale-up", Journal of Applied Electrochemistry 37 (2007), pp. 1107-1117.
Li, W., "Electrocatalytic Reduction of CO2 to Small Organic Molecule Fuels on Metal Catalysts", Advances in CO2 Conversion and Utilization (2010), pp. 55-76.
Liu, Y. et al., "Observation of surface structural changes of Pt octahedron nanoparticles and its effect in electrocatalysis oxidation of methanol", Catalysis Communications 10 (2009), pp. 1244-1247.
Liu, Z. et al., "General rules for predicting where a catalytic reaction should occur on metal surfaces: A density functional theory study of C-H and C-O bond breaking/making on flat, stepped, and kinked metal surfaces", Journal of the American Chemical Society 125 (2003), pp. 1958-1967.
Lopez-Cudero, A. et al., "CO electrooxidation on carbon supported platinum nanoparticles: Effect of aggregation", Journal of Electroanalytical Chemistry 644 (2010), pp. 117-126.
Lukaszewski, M. et al., "Electrosorption of carbon dioxide on platinum group metals and alloys-a review", Journal of Solid State Electrochemistry 13 (2009), pp. 813-827.
Lukaszewski, M. et al., "Comparative EQCM study on electrooxidation of carbon oxides adsorption products on noble metals and their alloys. Polycrystalline Pd-based systems", Journal of Electroanalytical Chemistry 606 (2007), pp. 117-133.
Ma, J. et al., "A short review of catalysis for CO2 conversion", Catal. Today 148 (2009), pp. 221-231.
Magdesieva, T.V. et al., "Lutetium monophthalocyanine and diphthalocyanine complexes and lithium naphthalocyanine as catalysts for electrochemical CO2 reduction", Journal of the Electrochemical Society 150 (2003), pp. E608-E612.
Maillard, F. et al., "Influence of particle agglomeration on the catalytic activity of carbon-supported Pt nanoparticles in CO monolayer oxidation", Physical Chemistry Chemical Physics 7 (2005), pp. 385-393.
Maillard, F. et al., "Size effects on reactivity of Pt nanoparticles in CO monolayer oxidation: The role of surface mobility", Faraday Discussions 125 (2004), pp. 357-377.
Masel, R., "Chemical Kinetics and Catalysis", Wiley (2001), pp. 702-742.
Meiwes-Broer, K., "Work functions of metal clusters", Hyperfine Interactions 89 (1994), pp. 263-269.
Morris, A. et al., "Electrocatalytic carbon dioxide activation: The rate-determining step of pyridinium-catalyzed CO2 reduction", Chem. Sus. Chem, 4 (2011), pp. 191-196.
Narayanan, R. et al., "Catalysis with transition metal nanoparticles in colloidal solution: Nanoparticle shape dependence and stability", Journal of Physical Chemistry B 109 (2005), pp. 12663-12676.
Noda, H. et al., "Electrochemical reduction of carbon dioxide at various metal electrodes in aqueous potassium hydrogen carbonate solution", Bull. Chem. Soc. Japan 63 (1990), pp. 2459-2462.
Ogura, K. et al., "CO2 attraction by specifically adsorbed anions and subsequent accelerated electrochemical reduction", Electrochimica Acta 56 (2010), pp. 381-386.
Ogura, K. et al., "Reduction of CO2 to ethylene at three-phase interface effects of electrode substrate and catalytic coating", Journal of the Electrochemical Society 152 (2005), pp. D213-D219.
Ogura, K. et al., "Selective formation of ethylene from CO2 by catalytic electrolysis at a three-phase interface", Prepr. Pap.—Am. Chem. Soc., Div. Fuel Chem. 49 (2004), pp. 9-10.
Ohya, S. et al., "Electrochemical reduction of CO2 in methanol with aid of CuO and Cu2O", Catalysis Today 148 (2009), pp. 329-334.
Oloman, C. et al., "Electrochemical processing of carbon dioxide", Chem. Sus. Chem. 1 (2008), pp. 385-391.

(56) References Cited

OTHER PUBLICATIONS

O'Mahony, A.M. et al., "The electrochemical reduction of hydrogen sulfide on platinum in several room temperature ionic liquids", The Journal of Physical Chemistry C112 (2008), pp. 7725-7730.

Pease, R.N. et al., "The catalytic combination of ethylene and hydrogen in the presence of metallic copper. III. Carbon monoxide as a catalyst poison", J. Am. Chem. Soc. 47 (1925), pp. 1235-1240.

Perez, E.R. et al., "In situ FT-IR and ex situ EPR analysis for the study of the electroreduction of carbon dioxide in N,N-dimethylformamide on a gold interface", Journal of Electroanalytical Chemistry 578 (2005), pp. 87-94.

Perez, J. et al., "Particle size effect for ethanol electro-oxidation on Pt/C catalysts in half-cell and in a single direct ethanol fuel cell", Journal of Electroanalytical Chemistry 654 (2011), pp. 108-115.

Photinon, K. et al., "Thick-Film carbon dioxide sensor via anodic adsorbate stripping technique and its structural dependence", Sensors 9 (2009), pp. 7203-7216.

Podlovchenko, B.I. et al., "Electroreduction of carbon dioxide on palladium electrodes at potentials higher than the reversible hydrogen potential", Journal of Electroanalytical Chemistry 373 (1994), pp. 185-187.

Popic, J.P. et al., "Reduction of carbon dioxide on ruthenium oxide and modified ruthenium oxide electrodes in 0.5 M NaHCO3", Journal of Electroanalytical Chemistry 421 (1997), pp. 105-110.

Qu, J. P. et al., "Electrochemical reduction of CO2 on RuO2/TiO2 nanotubes composite modified Pt electrode", Electrochimica Acta 50 (2005), pp. 3576-3580.

Raebiger, J.W. et al., "Electrochemical Reduction of CO2 to CO Catalyzed by a Bimetallic Palladium Complex", Organometallics 25 (2006), pp. 3345-3351.

Rakowski, M. et al., "Development of molecular electrocatalysts for CO2 reduction and H2 production/oxidation", Acc. Chem. Res. 42 (2009), pp. 1974-1982.

Ramirez, G. M. et al., "A supramolecular cobalt-porphyrin-modified electrode, toward the electroreduction of CO2", Journal of Coordination Chemistry 57 (2004), pp. 249-255.

Rezaei, B. et al., "Application of ionic liquids as an electrolyte additive on the electrochemical behavior of lead acid battery", Journal of Power Sources 187 (2009), pp. 605-612.

Rezaei, B. et al., "Effects of tetrabutylammonium hydrogen sulfate as an electrolyte additive on the electrochemical behavior of lead acid battery", Journal of Solid State Electrochemistry 12 (2008), pp. 1663-1671.

Rodriguez, P. et al., "Specific surface reactions for identification of platinum surface domains: Surface characterization and electrocatalytic tests", Electrochimica Acta 50 (2005), pp. 4308-4317.

Rosen, B. et al., "Ionic Liquid-Mediated Selective Conversion of CO2 to CO at Low Overpotentials", Science 334 (2011), pp. 643-644.

DEVICES AND PROCESSES FOR CARBON DIOXIDE CONVERSION INTO USEFUL FUELS AND CHEMICALS

CROSS-REFERENCE TO RELATED APPLICATION(S)

The present application is related to and claims priority benefits from U.S. Provisional Patent Application Ser. No. 61/705,042 filed Sep. 24, 2012, entitled "Devices And Processes For Carbon Dioxide Conversion Into Useful Fuels And Chemicals And Other Applications". The '042 provisional application is hereby incorporated herein by reference in its entirety.

The present application is also related to U.S. Non-Provisional patent application Ser. No. 12/830,338 filed Jul. 4, 2010, which claimed priority benefits from U.S. Provisional Patent Application Ser. No. 61/317,955 filed Mar. 26, 2010, both entitled "Novel Catalyst Mixtures". The present application is also related to International Application No. PCT/2011/030098 filed Mar. 25, 2011, entitled "Novel Catalyst Mixtures", which claimed priority benefits from the '955 provisional application and the '338 non-provisional application.

The present application is also related to U.S. Non-Provisional patent application Ser. No. 13/174,365 filed Jun. 30, 2011, which claimed priority benefits from U.S. Provisional Patent Application Ser. No. 61/484,072 filed May 9, 2011, both entitled "Novel Catalyst Mixtures". The present application is also related to International Patent Application No. PCT/2011/042809 filed Jul. 1, 2011, entitled "Novel Catalyst Mixtures", which claimed priority benefits from the '338 non-provisional application, the '098 international application, the '072 provisional application, and the '365 non-provisional application.

The present application is also related to U.S. Non-Provisional patent application Ser. No. 13/530,058 filed Jun. 21, 2012, entitled "Sensors for Carbon Dioxide and Other End Uses," which claimed priority benefits from U.S. Provisional Patent Application Ser. No. 61/499,225 filed Jun. 21, 2011, entitled "Low Cost Carbon Dioxide Sensors". The present application is also related to International Patent Application No. PCT/US2012/043651 filed Jun. 22, 2012, entitled "Low Cost Carbon Dioxide Sensors", which claimed priority benefits from the '255 provisional application.

The present application is also related to U.S. Provisional Patent Application Ser. No. 61/540,044 filed Sep. 28, 2011, entitled "On Demand Carbon Monoxide Generator for Therapeutic and Other Applications".

The present application is also related to U.S. Non-Provisional patent application Ser. No. 13/445,887 filed Apr. 12, 2012, entitled "Electrocatalysts for Carbon Dioxide Conversion", which claimed continuation-in-part status from the '338 non-provisional application. The '887 non-provisional application also claimed priority benefits from the '225 provisional application, the '044 provisional application, the '809 international application and the '098 international application.

Each of the above-referenced applications is hereby incorporated herein by reference in its entirety.

STATEMENT OF GOVERNMENT INTEREST

This invention was made, at least in part, with U.S. government support under U.S. Air Force contract No. FA8650-12-M-2249. The government has certain rights in the invention.

FIELD OF THE INVENTION

The field of the invention is electrochemistry. The devices and systems of this invention are applicable, for example, to the electrochemical conversion of carbon dioxide into useful products.

BACKGROUND OF THE INVENTION

There is a present need to decrease carbon dioxide ($CO_2$) emissions from industrial facilities. Over the years, a number of electrochemical processes have been suggested for the conversion of $CO_2$ into useful products. Processes for $CO_2$ conversion and the catalysts for them are discussed in U.S. Pat. Nos. 3,959,094, 4,240,882, 4,349,464, 4,523,981, 4,545,872, 4,595,465, 4,608,132, 4,608,133, 4,609,440, 4,609,441, 4,609,451, 4,620,906, 4,668,349, 4,673,473, 4,711,708, 4,756,807, 4,818,353, 5,064,733, 5,284,563, 5,382,332, 5,457,079, 5,709,789, 5,928,806, 5,952,540, 6,024,855, 6,660,680, 6,664,207, 6,987,134 (the '134 patent), 7,157,404, 7,378,561, 7,479,570, U.S. Patent Application Publication No. 2008/0223727 (the '727 application) and papers reviewed by Hori (Modern Aspects of Electrochemistry, 42, pages 89-189, 2008) ("the Hori Review"), Gattrell, et al. (Journal of Electroanalytical Chemistry, 594, pages 1-19, 2006) ("the Gattrell review"), and DuBois (Encyclopedia of Electrochemistry, 7a, pages 202-225, 2006) ("the DuBois review").

Generally an electrochemical cell contains an anode 50, a cathode 51 and an electrolyte 53 as indicated in FIG. 1. Catalysts are placed on the anode, and/or cathode, and/or in the electrolyte to promote desired chemical reactions. During operation, reactants or a solution containing reactants is fed into the cell. Then a voltage is applied between the anode and the cathode, to promote an electrochemical reaction.

When an electrochemical cell is used as a $CO_2$ conversion system, a reactant comprising $CO_2$, carbonate or bicarbonate is fed into the cell. A voltage is applied to the cell, and the $CO_2$ reacts to form new chemical compounds. Examples of cathode reactions in the Hori Review include $$CO_2 + 2e^- + 2H^+ \rightarrow CO + H_2O$$

$$2CO_2 + 2e^- \rightarrow CO + CO_3^{2-}$$

$$CO_2 + H_2O + 2e^- \rightarrow CO + 2OH^-$$

$$CO_2 + 2H_2O + 4e^- \rightarrow HCO^- + 3OH^-$$

$$CO_2 + 2H_2O + 2e^- \rightarrow H_2CO + 2OH^-$$

$$CO_2 + H_2O + 2e^- \rightarrow (HCO_2)^- + OH^-$$

$$CO_2 + 2H_2O + 2e^- \rightarrow H_2CO_2 + 2OH^-$$

$$CO_2 + 5H_2O + 6e^- \rightarrow CH_3OH + 6OH^-$$

$$CO_2 + 6H_2O + 8e^- \rightarrow CH_4 + 8OH^-$$

$$2CO_2 + 8H_2O + 12e^- \rightarrow C_2H_4 + 12OH^-$$

$$2CO_2 + 9H_2O + 12e^- \rightarrow CH_3CH_2OH + 12OH^-$$

$$2CO_2 + 6H_2O + 8e^- \rightarrow CH_3COOH + 8OH^-$$

$$2CO_2 + 5H_2O + 8e^- \rightarrow CH_3COO^- + 7OH^-$$

$$2CO_2 + 10H_2O + 14e^- \rightarrow C_2H_6 + 14OH^-$$

$$CO_2 + 2H^+ + 2e^- \rightarrow CO + H_2O, \text{ acetic acid, oxalic acid, oxylate}$$

$$CO_2 + 4H^+ + 4e^- \rightarrow CH_4 + O_2$$

where $e^-$ is an electron. The examples given above are merely illustrative and are not meant to be an exhaustive list of all possible cathode reactions.

Examples of reactions on the anode mentioned in the Hori Review include:

$$2O^{2-} \rightarrow O_2 + 4e^-$$

$$2CO_3^{2-} \rightarrow O_2 + 2CO_2 + 4e^-$$

$$4OH^- \rightarrow O_2 + 2H_2O + 4e^-$$

$$2H_2O \rightarrow O_2 + 4H^+ + 4e^-$$

The examples given above are merely illustrative and are not meant to be an exhaustive list of all possible anode reactions.

In the previous literature, catalysts comprising one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd have all shown activity for $CO_2$ conversion. Reviews include Hori (Modern Aspects of Electrochemistry, 42, pages 89-189, 2008) ("the Hori Review"), Gattrell, et al. (Journal of Electroanalytical Chemistry, 594, pages 1-19, 2006) ("the Gattrell review"), DuBois (Encyclopedia of Electrochemistry, 7a, pages 202-225, 2006) ("the DuBois review"), and the papers Li, et al. (Journal of Applied Electrochemistry, 36, pages 1105-1115, 2006, Li, et al. (Journal of Applied Electrochemistry, 37, pages 1107-1117, 2007) and Oloman, et al. (ChemSusChem, 1, pages 385-391, 2008) ("the Li and Oloman papers"), and references therein.

The results in the Hori Review show that the conversion of $CO_2$ is only mildly affected by solvent unless the solvent also acts as a reactant. Water can act like a reactant, so reactions in water are different than reactions in non-aqueous solutions. But the reactions are the same in most non-aqueous solvents, and importantly, the overpotentials are almost the same in water and in the non-aqueous solvents.

The catalysts have been in the form of either bulk materials, supported particles, collections of particles, small metal ions or organometallics.

Co-owned U.S. patent application Ser. Nos. 12/830,338 and 13/174,365, as well as International Application Nos. PCT/US2011/030098 and PCT/US2011/042809, disclose a catalyst mixture comprising an active metal and a Helper Catalyst capable of catalyzing $CO_2$ conversions with low overpotential and high electron conversion efficiency. However, the catalysts disclosed in these patent applications showed a lower activity than was desired.

The examples above consider applications for $CO_2$ conversion, but the present electrochemical device overcomes limitations of other systems. For example, some commercial $CO_2$ sensors use an electrochemical reaction to detect the presence of $CO_2$. At present, these sensors require over 1-5 watts of power, which is too high for portable sensing applications.

SUMMARY OF THE INVENTION

An electrochemical device converts $CO_2$ into other chemical reaction products. The pH at a point near the cathode catalyst is between 1.1 and 5.5, so that the device can overcome one or more of the limitations of low rates, high overpotentials and low electron conversion efficiencies (namely, selectivities), low rates for catalytic reactions and high power for sensors.

The device includes an electrochemical cell containing an anode 50, a cathode 51 and an electrolyte 53 as indicated in FIG. 1. Catalysts are placed on the anode, and/or cathode, and/or in the electrolyte to promote desired chemical reactions. There can be different electrolytes on different sides of a divided cell.

The electrolytes can be liquids, solids or gels. The device can be in the form of a membrane electrode assembly, a single or dual compartment cell or other design. The system can also include a catalytically active element, a Helper Catalyst, a hydrogen suppressor or other component.

Important to the design is the use of either an electrolyte, Helper Catalyst, liquid, solution, solid or Functional Unit near the cathode with a Moderate Acidity. The electrolyte, Helper Catalyst or Helper Catalyst solution can be in the form of a solid electrolyte, liquid electrolyte, or a gel.

The device can also include any of (i) a catalytically active metal, (ii) a separating membrane, (iii) a Helper Catalyst, (iv) a solid membrane between the anode and cathode, (v) gas diffusion layers, (vi) channels for gas and/or liquid flow, and (vii) a stack of several electrochemical cells.

DETAILED DESCRIPTION OF PREFERRED EMBODIMENT(S)

Figure 1:
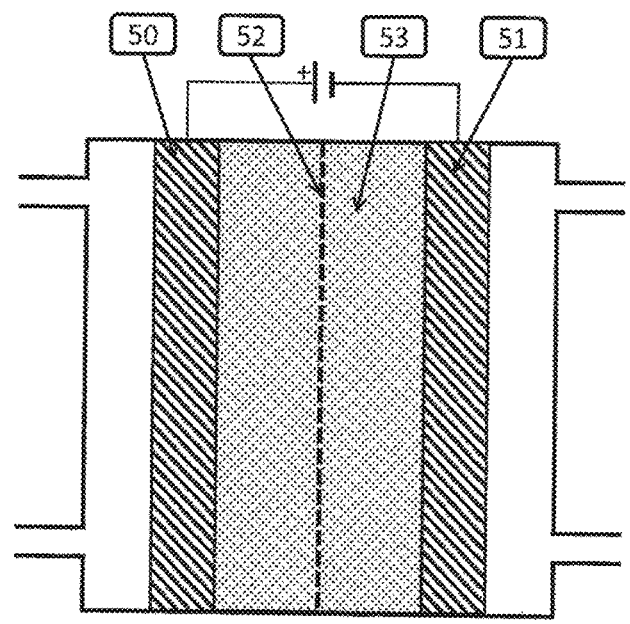
FIG. 1 is a diagram of a typical electrochemical cell.

It is understood that the invention is not limited to the particular methodology, protocols and reagents described herein, as these can vary as persons familiar with the technology involved here will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. Thus, for example, a reference to "a linker" is a reference to one or more linkers and equivalents thereof known to those skilled in the art. Similarly, the phrase "and/or" is used to indicate one or both stated cases can occur, for example A and/or B includes (A and B) and (A or B).

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment can be employed with other embodiments as the skilled artisan would recognize, even if not explicitly stated herein.

Any numerical value ranges recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 98, specifically from 20 to 80, more specifically from 30 to 70, it is intended that values such as 15 to 85, 22 to 68, 43 to 51, 30 to 32 and the like, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value are to be treated in a similar manner.

Moreover, provided immediately below is a "Definitions" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

DEFINITIONS

The term "electrochemical conversion of $CO_2$" as used here refers to any electrochemical process where carbon dioxide, carbonate, or bicarbonate is converted into another chemical substance in any step of the process.

The term "CV" as used here refers to a cyclic voltammogram or cyclic voltammetry.

The term "Overpotential" as used here refers to the potential (voltage) difference between a reaction's thermodynamically determined reduction or oxidation potential and the potential at which the event is experimentally observed.

The term "Cathode Overpotential" as used here refers to the overpotential on the cathode of an electrochemical cell.

The term "Anode Overpotential" as used here refers to the overpotential on the anode of an electrochemical cell.

The term "Electron Conversion Efficiency" also called "Faradaic Efficiency" as used here refers to the selectivity of an electrochemical reaction. More precisely, it is defined as the fraction of the current that is supplied to the cell that goes to the production of a desired product.

The term "Catalytically Active Element" as used here refers to any chemical element that can serve as a catalyst for the electrochemical conversion of $CO_2$.

The term "Helper Catalyst" as used here refers to any organic molecule or ion, or a mixture of organic molecules and/or ions, that does at least one of the following:
 (a) speeds up a chemical reaction, or
 (b) lowers the overpotential of the reaction,
without being substantially consumed in the process.

The term "Helper Catalyst" does not include organo-metallic compounds.

The term "Active Element, Helper Catalyst Mixture" as used here refers to any mixture that includes one or more Catalytically Active Element(s) and at least one Helper Catalyst.

The term "Ionic Liquid" as used here refers to salts or ionic compounds that form stable liquids at temperatures below 200° C.

The term "Deep Eutectic Solvent" as used here refers to an ionic solvent that includes a mixture which forms a eutectic with a melting point lower than that of the individual components.

The term "EMIM" as used here refers to 1-ethyl-3-methylimidazolium cations.

The term "EMIM-BF4" as used here refers 1-ethyl-3-methylimidazolium tetrafluoroborate.

The term "QRE" as used here refers to a quasi-reference electrode.

The term "Ag-QRE" as used here refers to a silver quasi reference electrode.

The term "potential of the peak" as used here refers to the potential where the absolute value of the current is maximized.

The term "ionomer" as used here refers to a polymer that includes ionized repeating units and can include electrically neutral repeating units, The term "Syngas" as used here refers to a mixture including CO and hydrogen wherein the CO and $H_2$ concentrations are each at least 10% by mole.

The term "Hydrogen Evolution Reaction" also called "HER" as used here refers to the electrochemical reaction $2H^+ + 2e^- \rightarrow H_2$.

The term "SHE" as used here refers to the potential of the standard hydrogen electrode.

The term "MEA" as used here refers to a membrane electrode assembly.

The term "NSTF" as used here refers to a 3M Company proprietary nano-structured thin film platinum catalyst.

The term "Buffer Layer" as used here refers to an ion conducting layer that lies between the cathode catalyst and the membrane in an MEA or electrochemical device. The Buffer Layer can include solid, liquid, gel or mixtures of these. It could also be a binder used to hold the cathode catalyst onto the cathode.

The term "Functional Unit" as used here refers to a piece of a polymer chain. The term specifically includes the monomers that can be used to synthesize the polymer chain, scission fragments of the polymer chain and oligomers made from the same monomers as the polymer chain.

The term "Moderately Acidic" or "Moderate Acidity" is used to indicate a substance that satisfies at least one of the following tests:
 (i) Measure the pH of the substance, and determine that the pH is between 1.1 and 5.5.

(ii) Mix a given volume of the substance with an equal volume of water and stir thoroughly, measure the pH of the resultant water rich phase, and determine that the pH of the resultant water rich phase is between 1.1 and 5.5.

(iii) Mix a given volume of the substance with an equal volume of isopropanol and stir thoroughly, measure the pH of the resultant alcohol rich phase, and determine that the pH of the resultant alcohol rich phase is between 1.1 and 5.5.

(iv) Add 20% water by volume to the alcohol rich phase, measure the pH of the resultant alcohol rich phase, and determine that the pH of the resultant alcohol rich phase is between 1.1 and 5.5.

Specific Description

The present electrochemical device includes an anode, a cathode, an electrolyte, and at least one of:
(a) a Helper Catalyst;
(b) a solution;
(c) a liquid;
(d) a solid; and
(e) a Functional Unit, either touching or within 1 mm of the cathode or the cathode catalyst, wherein the electrolyte, Helper Catalyst, solution, liquid, solid or Functional Unit satisfies one of the following criteria:
(i) it is Moderately Acidic, or
(ii) it contains between 1 and 98% water by volume.

The present electrochemical device includes at least one of an electrolyte, a Helper Catalyst, a solution, a liquid, a solid, or a Functional Unit that meets at least of the following tests:
(a) Measure the pH of the substance, and determine that the pH is between 1.1 and 5.5.
(b) Mix a given volume of the substance with an equal volume of water and stir thoroughly, measure the pH of the resultant water rich phase, and determine that the pH of the resultant water rich phase is between 1.1 and 5.5.
(c) Mix a given volume of the substance with an equal volume of isopropanol and stir thoroughly, measure the pH of the resultant alcohol rich phase, and determine that the pH of the resultant alcohol rich phase is between 1.1 and 5.5.
(d) Add 20% water by volume to the alcohol rich phase, measure the pH of the resultant alcohol rich phase, and determine that the pH of the resultant alcohol rich phase is between 1.1 and 5.5.

The device can also include Catalytically Active Elements. In particular the devices can include one or more of the following Catalytically Active Elements: V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd, Preferred Catalytically Active Elements include: Pt, Pd, Au, Ag, Cu, Ni, Fe, Co, Ru and Rh. Most preferred Catalytically Active Elements include Au, Ag, and Cu.

The device can also include Helper Catalysts, ionic liquids, ionic liquid gels, deep eutectic solvents, amines, and/or phosphines, including specifically imidazoliums (also called imidazoniums), pyridiniums, pyrrolidiniums, phosphoniums, ammoniums, sulfoniums, prolinates, methioninates, acetocholines (also called acetylcholines), alanines, aminoacetonitriles, methylammoniums, arginines, aspartic acids, cholines, threonines, chloroformamidiniums, thiouroniums, quinoliniums, pyrrolidinols, serinols, benzamidines, sulfamates, acetates, carbamates, triflates, and cyanides.

The products of the reaction can include: $CO$, $HCO^-$, $H_2CO$, $(HCO_2)^-$, $H_2CO_2$, $CH_3OH$, $CH_4$, $C_2H_4$, $CH_3CH_2OH$, $CH_3COO^-$, $CH_3COOH$, $C_2H_6$, $(COOH)_2$, $(COO^-)_2$, $H_2C=CHCOOH$, $CF_3COOH$, other organic acids, carbonates, di-phenyl carbonate, and polycarbonates. This is by no means a complete list of possible products.

The device can also include a Hydrogen Suppressor including at least one constituent selected from the group consisting of choline chlorine, other choline salts, tetrabutylammonium hydrogen sulfate (TBAHS), ethylenediaminetetraacetic acid (EDTA), benzaldehyde and substituted benzaldehydes, di-acids such as succinic acid and substituted di-acids, an ionic liquid and a compound of the form $R_1R_2R_3N^+(CH_2)_nOH$, $R_1R_2R_3N^+(CH_2)_1COH$ or $R_1R_2R_3N^+(CH_2)_1COOH$ wherein n=1-4 and $R_1$, $R_2$ and $R_3$ are each a ligand containing at least 1 carbon atom.

The present electrochemical device can be utilized in systems that include fuel cells, sensors, $CO_2$ remediation devices and systems, and systems that convert $CO_2$ into useful products.

Without further elaboration, it is believed that persons familiar with the technology involved here using the preceding description can utilize the invention to the fullest extent. The following examples are illustrative only, and are not meant to be an exhaustive list of all possible embodiments, applications or modifications of the invention.

EXAMPLE 1

The Effects of pH on the Efficiency of $CO_2$ Conversion

The experiment used the flow cell described in Rosen et al., Science, 334, pages 643-644, 2011. It was a sandwich style reactor in which there were two liquid channels containing the catholyte and anolyte, and one $CO_2$ gas channel. The gas channel was made of aluminum and was also the cathodic current collector. Just below the cathodic current collector was a piece of graphite gas diffusion layer (available from SGL Carbon LLC, Charlotte, N.C., USA, under the trade designation SIGRACET) in which 10 mg of silver nanoparticles were made into an ink and painted onto an area of 1.5 cm². The ink was made by mixing 10 mg of silver nanopowder (>100 nm diameter, Aldrich) with 600 μl of 18.2Ω ultra-pure water, 600 μl of isopropyl alcohol, and 10 μl of a 5% solution of 1100EW perfluorosulfonic acid polymer, available under the trade designation NAFION from DuPont, Wilmington, Del. This mixture was then sonicated for 2 min. The platinum anode ink was made the exact same way except using high surface area platinum black nanoparticles (Alfa Aesar) in lieu of silver. Below the cathode was a liquid channel made of fluoropolymer available under the trade designation TEFLON (DuPont) in which the ionic liquid mixtures could come in contact with the cathode. Below the top liquid channel was a 2 cm² piece of NAFION-117 membrane (DuPont). Below the membrane is the lower liquid channel where 0.1 M $H_2SO_4$ passed over the anode. The gas channel exit was connected to an SRI Gas Chromatograph (SRI Instruments, Torrance, Calif., USA) equipped with a 6-foot Molecular Sieve 5A column and a thermal conductivity detector (TCD). The column was kept at 100° C. while the detector was at 110° C. The gas chromatograph (GC) utilized a helium carrier gas with a flow rate of 25 sccm.

During the experiments, 5 ml/min of mixtures of EMIM-BF4 and water or EMIM-BF4 and 0.5 M $H_2SO_4$ were fed into the cathode liquid channel, and 5 ml/min of 0.1 M $H_2SO_4$ was fed into the anode liquid channel. The cathode was held at −0.7 V with respect to SHE. 5 sccm of $CO_2$ was fed into the gas channel and the rates of CO and hydrogen production were measured with the GC.

Figure 2:
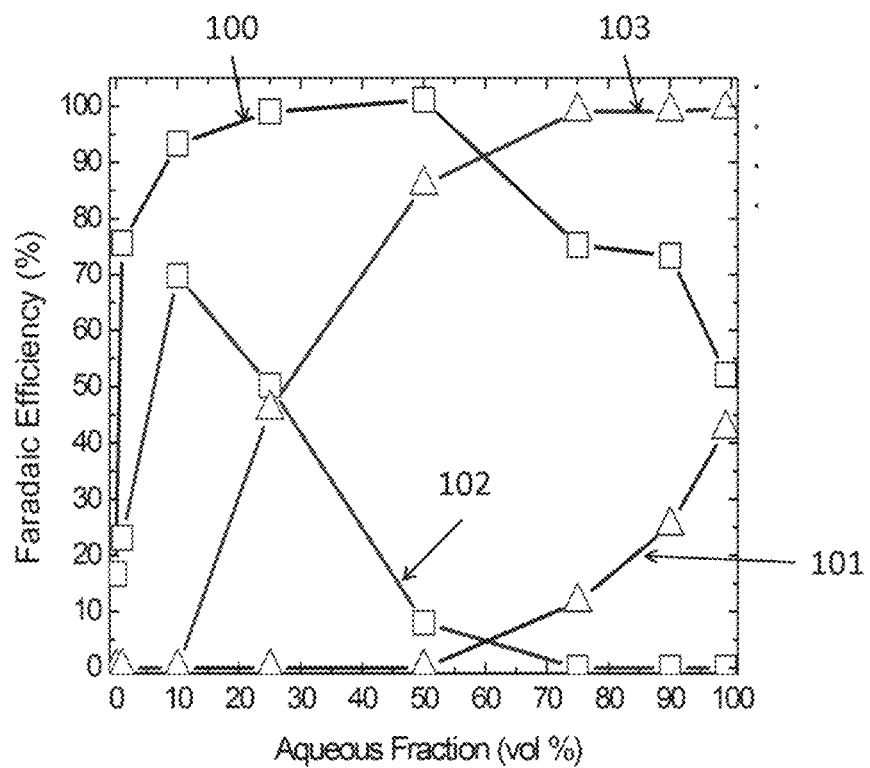
FIG. 2 is a plot showing the effect of diluting the EMIM $BF_4$ in the cathode flow channel with water $H_2O$ (100 and 101) or 0.5 M $H_2SO_4$ (102 and 103) on the Faradaic efficiency of $CO_2$ reduction to CO (100 and 102) and $H_2$ (101 and 103).

FIG. 2 shows how the Faradaic efficiency for CO and $H_2$ formation varied as a function of the volume fraction of water in the Water/EMIM-BF4 mixture. In each case the EMIM-BF4 mixture was prepared at least 24 hours in advance, because it was found unexpectedly that the rate was higher and the pH was lower when the EMIM-BF4 solution was prepared in advance than when a fresh solution was used. It was found that the Faradaic efficiency of the process was low in pure EMIM-BF4, but the Faradaic efficiency for $CO_2$ formation increased rapidly when as little 1% by volume water was added to the mixture. The Faradaic efficiency stayed high up to 90% water by volume, but dropped to unacceptable levels when 100% water was used. FIG. 2 also shows that the optimum water content was between 10 and 70% for pure CO formation, and between 70 and 98% if the objective was to produce syngas.

FIG. 2 also shows the effect of diluting the EMIM-BF4 on the cathode liquid channel with 0.1 M $H_2SO_4$. In this case syngas was produced when there was between 1 and 50% by volume of 0.5 M $H_2SO_4$. Only hydrogen was observed at higher volumes of 0.5 M $H_2SO_4$.

Figure 3:
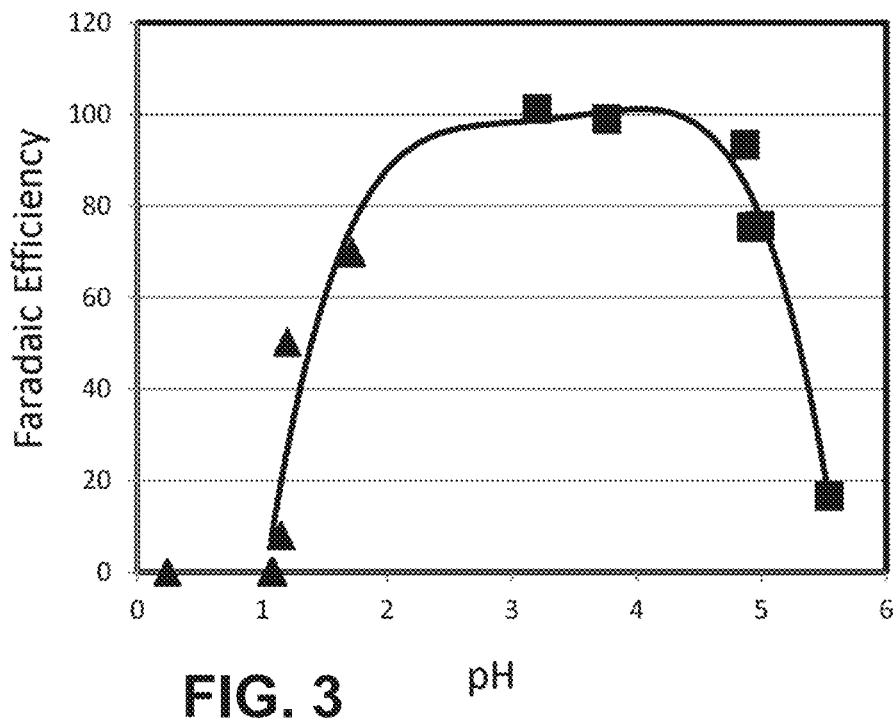
FIG. 3 is a plot of the Faradaic efficiency of $CO_2$ conversion to CO, plotted as a function of the pH of the mixture. The triangles were measured by diluting the EMIM-BF4 with 0.5 M sulfuric acid; the square points were measured by diluting the EMIM-BF4 with water.

FIG. 3 shows a replot of the same data in FIG. 2 as a function of the pH in the aged solution. Notice that pure CO was formed at high rates when the pH was between 5.5 and 2.5. Syngas was formed when the pH was between 2.5 and 1.1. It was also found that the optimal pH for CO formation was between 2.5 and 5 while the optimum pH for syngas formation was between 1.2 and 1.8.

It is useful to put the results in FIGS. 2 and 3 into the context of the literature. The Hori Review teaches that $CO_2$ conversion catalysts work best when the solution is near neutral (namely, pH 6-7). According to the Hori Review, "The hydrogen reduction reaction HER is prevalent particularly in acidic solutions, whereas $CO_2$ molecules do not exist in a basic solution". Consequently the Hori Review notes "most of $CO_2$ reduction studies were done with neutral electrolyte solutions" (namely, pH 7). The pH changes to when $CO_2$ is absorbed.

The data in FIG. 3 shows that in the presence of ionic liquids, solutions with a pH of 6-7 are not preferred. Instead the optimal pH is between 1.1 and 5.5.

It was also noted that fresh EMIM-BF4/water solutions show a pH near 7. The pH is in the optimal range only when aged solutions are used. Another unexpected finding in the data in FIG. 2 is that when water was added, the CO production efficiency increased and no significant hydrogen formation was observed. By comparison, Tomita et al., Journal of the Electrochemical Society 147, pages 4164-4167 (2000), examined the effects of water additions on $CO_2$ electrolysis in acetonitrile-water mixtures, and found that they could observe significant hydrogen formation when as little as 0.01 moles/liter of water is added to a dry acetonitrile solution. Hydrogen formation dominates at water concentrations of 1 moles/liter or more. Here, little hydrogen formation was found when the water concentration is about 25 moles/liter and significant hydrogen formation was only observed at water concentrations above 30 moles/liter. Interestingly, about the same amount of hydrogen was produced at a water concentration of 37 moles/liter as Tomita et al. reported at a water concentration of 0.03 moles/liter. Clearly, the EMIM-BF4 can inhibit hydrogen formation.

EXAMPLE 2

Tests in an Electrochemical Cell

Tests were also performed in an electrochemical cell. The experiments were conducted in a custom made three electrode electrochemical cell described in Rosen et al., The Journal of Physical Chemistry C 116, pages 15307-15312 (2012). The working electrodes were <100 nm silver nanoparticle catalyst (Sigma Aldrich) supported on a 5 mm diameter gold slug. The counter electrode was made of a 25×25 mm piece of platinum gauze purchased through Alfa Aesar. The gauze was connected to a 5 inch (12.7 cm) long 0.5 mm diameter platinum wire. The reference electrode was a silver quasi-reference electrode (Ag-QRE).

During the experiment, EMIM-BF4 was mixed with 0.001 M sulfuric acid to produce a mixture with a known pH. The mixture was loaded in the cell and sparged with argon to remove any residual $CO_2$. Then the potential of the working electrode was held constant at −1.2, −1.3, −1.4 and −1.5 V with respect to the Ag-QRE and the current was recorded as a function of time. Generally the current showed a rapid decrease in the first few seconds, reaching a steady state value in 5 to 10 seconds. The average steady state value over the next 2 minutes was recorded. Next, the solution was saturated with $CO_2$ and a second steady state value was recorded. The current due to $CO_2$ conversion, namely, the difference between the current in the presence and absence of $CO_2$, was then calculated.

Figure 4:
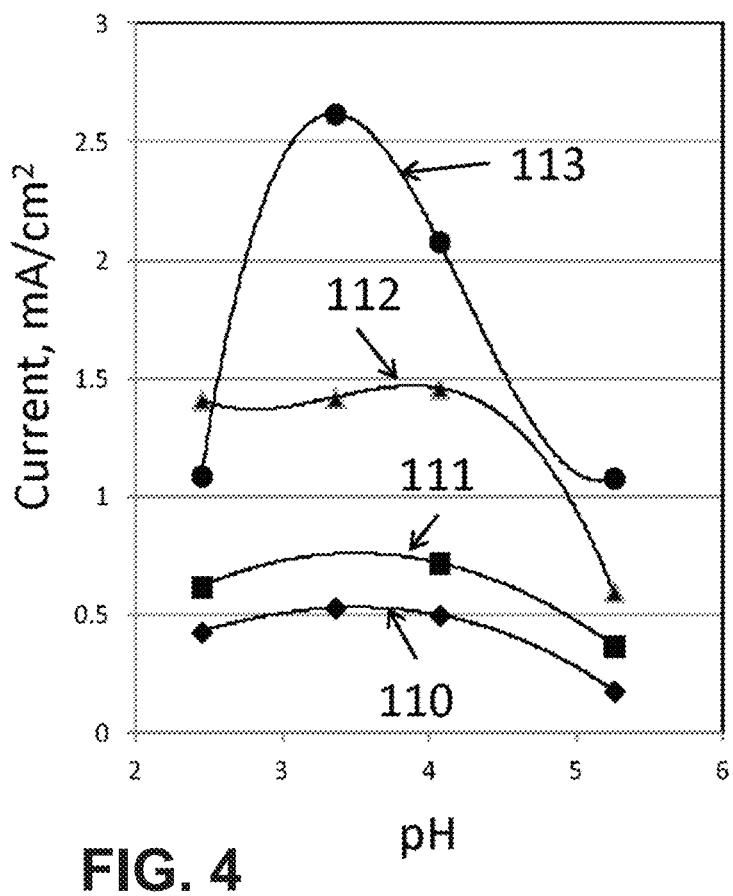
FIG. 4 shows the $CO_2$ conversion current as a function of pH measured in a three electrode electrochemical cell at 1.2 V (110), 1.3 V (111), 1.4 V (112) and 1.5 V (113).

FIG. 4 shows how the current due to $CO_2$ conversion varied with the pH at different applied potentials. Notice that the $CO_2$ conversion current reached a maximum at a pH between 2 and 4.

Again it should be noted that the Hori Review suggests that the optimal pH for $CO_2$ conversion is between 6 and 7. The data in FIG. 4 shows that in the presence of ionic liquids, solutions with a pH of 6-7 are not preferred. Instead the optimal pH for $CO_2$ conversion on silver is between 2.2 and 4.

EXAMPLE 3

Extension to Platinum

The objective of this example is to demonstrate that the present electrochemical device also operates with a platinum catalyst. The experiments were conducted in a custom made three electrode electrochemical cell described in Rosen et al., The Journal of Physical Chemistry C 116, pages 15307-15312 (2012). Prior to sparging any gases into an electrochemical cell, the gases were sent through a tube of Drierite, anhydrous calcium sulfate (W.A. Hammond Drierite Co. Ltd.), in order to remove any residual moisture present in the gas streams. Working electrodes were high surface area platinum black (Alfa Aesar) supported on a 5 mm diameter platinum slug. The counter electrode was made of a 25×25 mm piece of platinum gauze purchased through Alfa Aesar. The gauze was connected to a 5 inch (12.7 cm) long 0.5 mm diameter platinum wire. The reference electrode was an Ag/0.01 M $Ag^+$ non aqueous reference electrode (BASi, Bioanalytical Systems Inc., West Lafayette, Ind., USA). The reference electrode was calibrated using the Ferrocene/Ferrocene+ couple as an internal standard. During the experiments, a Solartron SI 1287 potentiostat (Solartron Analytical, Oak Ridge, Tenn., USA) was used to hold the potential of the working electrode constant at −0.7 V with respect to SHE for 5 minutes, then the potential was raised at 10 mV/min and the area of the CO stripping peak associated with $CO_2$ conversion to CO was measured.

Figure 5:
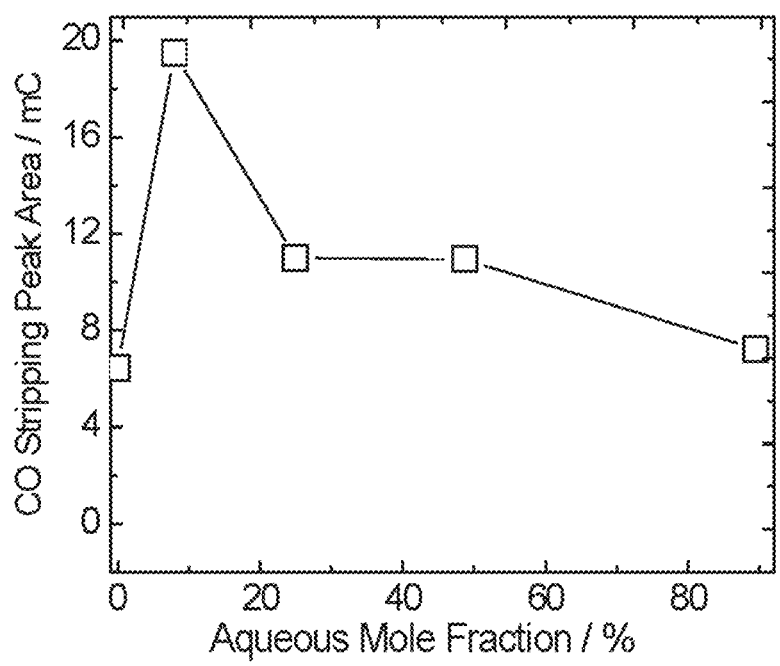
FIG. 5 illustrates the effect of adding $H_2O$ on the CO striping peak area, measured by holding a platinum electrode at a reducing potential of –0.7 V vs. SHE for 5 min and then ramping the voltage at 10 mV/min.

FIG. 5 shows how the CO stripping peak varied with the water content. Notice that the $CO_2$ stripping peak reached a maximum with about 12% by mole (1% by volume) water. This corresponds to a pH of 5. The data in FIG. 5 shows that in the presence of ionic liquids, solutions with a pH of 6-7 are not preferred. Instead the optimal pH for $CO_2$ conversion on platinum in ionic liquids is about 5.

EXAMPLE 4

Application of the Present Electrochemical Device in an MEA

Figure 6:
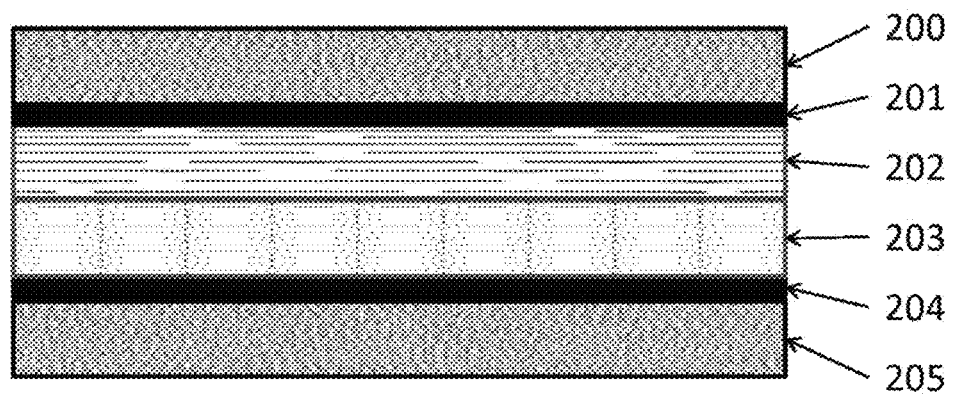
FIG. 6 is a cross-section of an MEA that includes a cathode 200, a cathode catalyst 201, a Buffer Layer 202 that is Moderately Acidic, an ionomer membrane 203, an anode catalyst 204, and an anode 205.

The examples above used liquid solutions, but in some applications one might want membrane electrode assemblies (MEAs) instead. FIG. 6 shows a possible structure of the MEA. It includes a cathode 200, a cathode catalyst 201, Buffer Layer 202 that is Moderately Acidic, an ionomer membrane 203, an anode catalyst 204, and an anode 205. The objective of this example is to determine whether such a structure would be active for $CO_2$ conversion.

The MEA was constructed using a SIGRACET graphite gas diffusion layer cathode. 10 mg of silver nanoparticles were made into an ink and painted onto an area of 1.5 $cm^2$ on the cathode as described in Example 1. Next a Buffer Layer was constructed by saturating a paper towel with a 50/50 mixture by volume of EMIM-Cl and water. Third, a NAFION-117 membrane coated with 3M platinum NSTF catalyst on one side was obtained from 3M Company, St. Paul, Minn., USA. It served as the proton transfer membrane and the anode catalyst. A SIGRACET graphite gas diffusion layer anode was added as the anode, and the parts were sandwiched together to form an MEA. The liquid channels were removed from the flow cell used to take the data in Example 1, and the MEA was mounted in the cell. A potential of 2.5 V was applied to the cell, and the current was measured with either nitrogen or $CO_2$ being fed to the cathode at 5 sccm.

Figure 7:
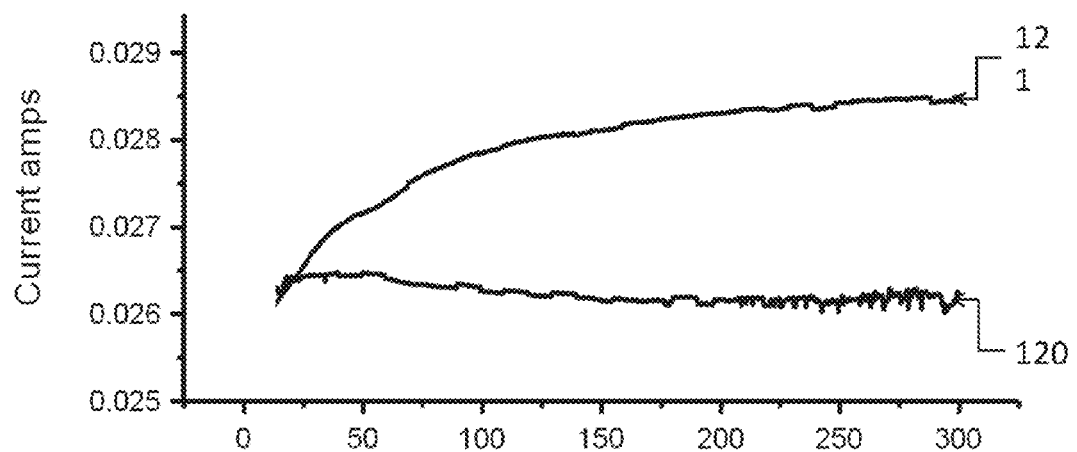
FIG. 7 is a graph of the current produced when the MEA prepared as in example 4 is exposed to nitrogen (120) and when the MEA is exposed to $CO_2$ (121)

FIG. 7 shows the currents produced. Notice that the current is higher in $CO_2$ showing that a MEA with a Buffer Layer including a substance with a pH between 1 and 5 is effective for $CO_2$ conversion.

The results in FIG. 7 show that the device with a MEA similar to that in FIG. 6, with a Moderately Acidic Buffer Layer is also useful as a component in a sensor, since the current is different in $CO_2$ and in $N_2$.

Figure 8:
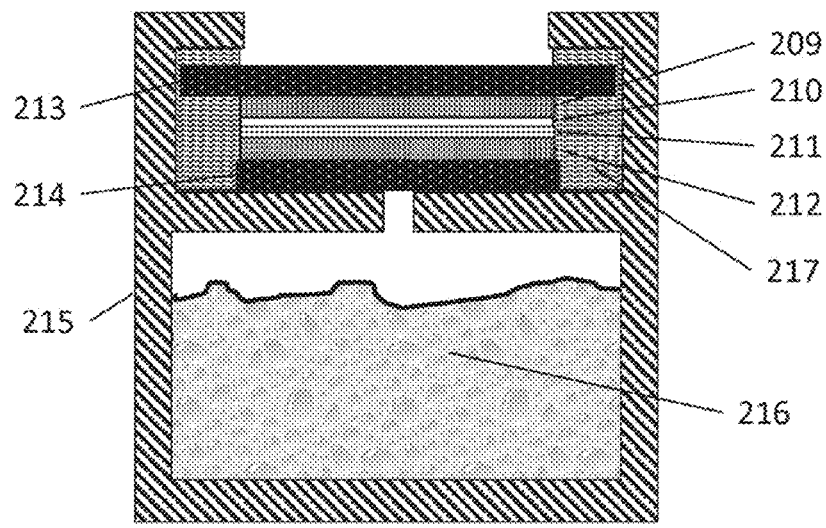
FIG. 8 is a cross-section diagram of a sensor comprising a membrane electrode assembly (MEA) that includes a working electrode 209, a Buffer Layer 210, a proton conducting membrane 211 and a counter electrode 212. The MEA is sandwiched between two current collectors 213 and 214. The device sits in a housing 215 which can include a water reservoir 216. There also is an insulating structure 217 to keep the anode from shorting to the housing.

FIG. 8 shows one possible design of the device. It consists of an MEA in a container, with current collectors and insulators, and, importantly, a Buffer Layer between the anode and cathode.

Figure 9:
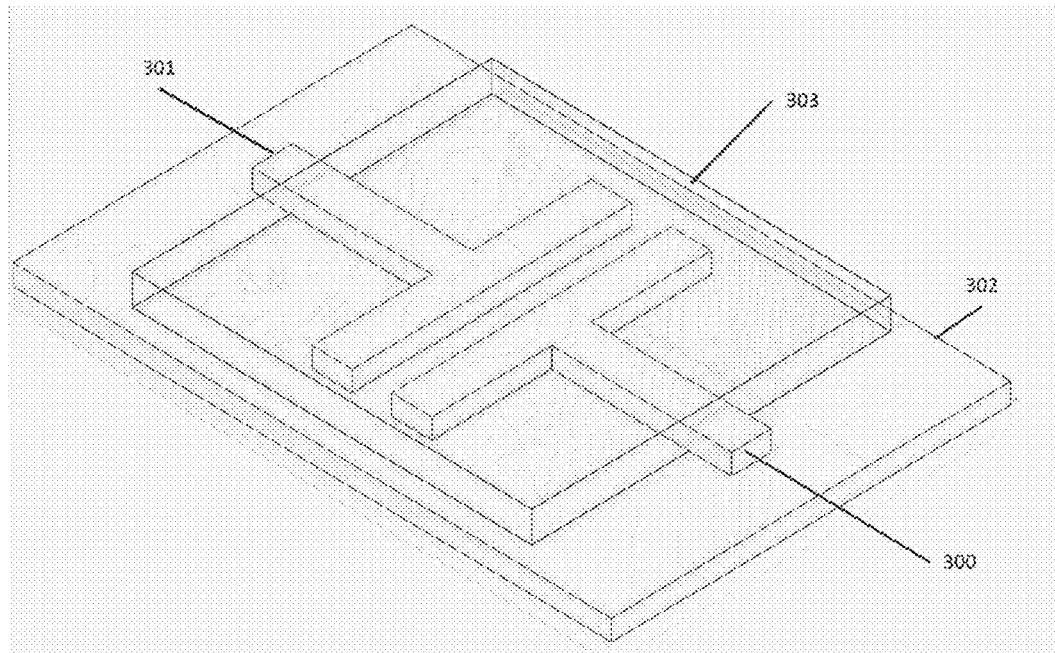
FIG. 9 is a diagram of an alternate sensor, which consists of an anode 300, a cathode 301, on a substrate 302. Parts of the anode and cathode are covered by an electrolyte 303.

FIG. 9 shows an alternate design for the sensor. It consists of an anode 300, cathode 301, on a substrate 302. Parts of the cathode are covered by an electrolyte 303 that is Moderately Acidic.

Figure 10:
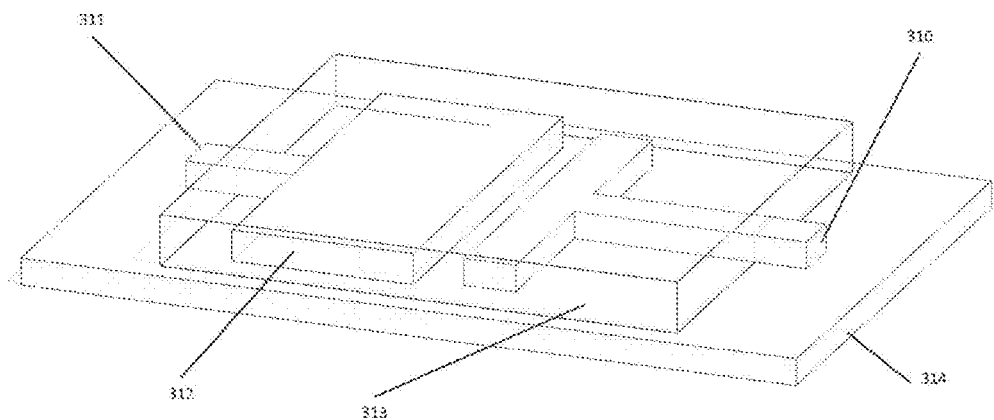
FIG. 10 is a diagram of yet another alternate sensor, which consists of an anode 310, a cathode 311, on a substrate 314. Part of the cathode is covered by a Buffer Layer 312, and then there is an electrolyte 313 connecting the Buffer Layer to the anode.

FIG. 10 is a diagram of yet another alternate sensor design. It consists of an anode 310, cathode 311, on a substrate 314. Part of the cathode is covered by a Buffer Layer 312 that is Moderately Acidic. An electrolyte 313 connects Buffer Layer 312 to anode 310.

FIGS. 9 and 10 show simple sensor geometries. However, the present electrochemical device is not limited to the specific geometry shown. Instead the important feature is the presence of a Moderately Acidic Buffer Layer or electrolyte touching, or within 1 mm of, the cathode.

The examples given above are merely illustrative and are not meant to be an exhaustive list of all possible embodiments, applications or modifications of the present electrochemical device. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

What is claimed is:

1. An electrochemical device for converting $CO_2$ to a reaction product, the electrochemical device comprising a cathode, a source of $CO_2$ in fluid communication with the cathode, a Helper Catalyst, and a component located within 1 mm of the cathode, wherein the Helper Catalyst is any organic molecule or ion, or a mixture of organic molecules and/or ions, excluding organo-metallic compounds, that does at least one of the following:
   (i) speeds up a chemical reaction, or
   (ii) lowers the overpotential of the reaction,
   without being substantially consumed in the process,
   the component comprising at least one of:
   (a) an electrolyte;
   (b) the Helper Catalyst;
   (c) a solution;
   (d) a liquid;
   (e) a Functional Unit of a polymer chain; and
   (f) a solid,
wherein the component comprises a substance having a pH having a value of 1.1-5.5 when the pH of the substance is measured according to at least one of the following tests:
   Test I: measuring the pH of the substance directly, using a pH meter;
   Test II: mixing a given volume of the substance with an equal volume of water and agitating, then measuring the pH of the resultant water-rich phase;
   Test III: mixing a given volume of the substance with an equal volume of isopropanol and stirring, then measuring the pH of the resultant alcohol-rich phase; and
   Test IV: mixing a given volume of the substance with an equal volume of isopropanol and agitating, adding 20% water by volume to the alcohol-rich phase, then measuring the pH of the resultant alcohol-rich phase.

2. The electrochemical device of claim 1, wherein the pH of the substance is 2-5.

3. The electrochemical device of claim 2, wherein the pH of the substance is 2.5-4.0.

4. The electrochemical device of claim 1, wherein the pH of the substance is 1.2-1.8.

5. The electrochemical device of claim 1, wherein at least one of the electrolyte, liquid, solid or solution has a concentration of 1%-98% water by volume.

6. The electrochemical device of claim 5, wherein at least one of the electrolyte, liquid, solid and solution has a concentration of 10%-70% water by volume.

7. The electrochemical device of claim 5, wherein at least one of the electrolyte, liquid, solid and solution has a concentration of 70%-98% water by volume.

8. The electrochemical device of claim 1, further comprising a membrane electrode assembly, the membrane electrode assembly comprising:
   (i) the cathode;
   (ii) a cathode catalyst;
   (iii) an ion conducting Buffer Layer;
   (iv) a separator membrane;
   (v) an anode catalyst; and
   (vi) an anode.

9. The electrochemical device of claim 8, wherein the Buffer Layer is located within 1 mm of the cathode, the Buffer Layer comprising a substance having a pH of 1.1-5.5 when measured according to at least one of the tests listed in claim 1.

10. The electrochemical device of claim 1, wherein at least one of the cathode and a catalyst operatively associated with the cathode comprises a catalytically active element.

11. The electrochemical device of claim 10, wherein the catalytically active element comprises at least one of V, Cr, Mn, Fe, Co, Ni, Cu, Zr, Nb, Mo, Ru, Rh, Pd, Ag, Cd, W, Re, Ir, Pt, Au, Hg, Pb and Bi.

12. The electrochemical device of claim 11, wherein the catalytically active element comprises at least one of Pt, Pd, Au, Ag, Cu, Ni, Fe, Co, Ru and Rh.

13. The electrochemical device of claim 12, wherein the catalytically active element comprises Ag.

14. The electrochemical device of claim 1, wherein the Helper Catalyst comprises at least one of an organic cation and an organic anion.

15. The electrochemical device of claim 1, wherein the Helper Catalyst comprises at least one of a phosphine, an imidazolium, a pyridinium, a pyrrolidinium, a phosphonium, a sulfonium, a prolinate, a methioninate and a choline.

16. The electrochemical device of claim 15, wherein the choline comprises one of a choline salt and a choline ester salt.

17. The electrochemical device of claim 15, wherein the Helper Catalyst comprises at least one of a choline and a 1-ethyl-3-methylimidazolium cation.

18. The electrochemical device of claim 1, wherein the Helper Catalyst comprises a tetrafluoroborate anion.

19. The electrochemical device of claim 1, wherein the reaction product comprises one of a carbonate and an organic acid.

20. The electrochemical device of claim 1, wherein the reaction product comprises at least one of $CO$, $HCO^-$, $H_2CO$, $(HCO_2)^-$, $HCOOH$, $CH_3OH$, $CH_4$, $C_2H_4$, $CH_3CH_2OH$, $CH_3COO^-$, $CH_3COOH$, $C_2H_6$, $(COOH)_2$, $(COO^-)_2$, $CH_2$=$CHCOOH$, $CF_3COOH$ and $(C_6H_5O)_2CO$.

21. The electrochemical device of claim 20, wherein the reaction product comprises at least one of CO and HCOOH.

22. A $CO_2$ sensor comprising the electrochemical device of claim 1.

23. A process for making a reaction product, the process comprising:
   introducing at least one of $CO_2$, a carbonate and a bicarbonate to the cathode of the electrochemical device of claim 1, and
   applying electrical energy to the electrochemical device to effect electrochemical conversion of the at least one of $CO_2$, a carbonate and a bicarbonate to the reaction product.

24. The process of claim 23, wherein the reaction product comprises at least one of CO, HCOOH, $CH_2$=$CHCOOH$ and $(C_6H_5O)_2CO$.

25. The process of claim 23, wherein the Helper Catalyst of the electrochemical device functions as at least one of a solvent, an electrolyte and an additive.

* * * * *